United States Patent
Suh et al.

(10) Patent No.: US 9,879,226 B2
(45) Date of Patent: Jan. 30, 2018

(54) MESENCHYMAL STEM CELL BASIC CULTURING MEDIUM

(75) Inventors: Dong-Sam Suh, Seoul (KR); Jun Keun Lee, Seoul (KR); Dong Il Chang, Seoul (KR); Min Jung Choi, Bucheon-si (KR); Jang Hoon Kim, Seoul (KR); Ga Ram Kim, Seoul (KR); Cheong Ho Chang, Seoul (KR)

(73) Assignee: SEWON CELLONTECH CO., LTD., Seoul (KR)

( * ) Notice: Subject to any disclaimer, the term of this patent is extended or adjusted under 35 U.S.C. 154(b) by 185 days.

(21) Appl. No.: 14/241,393

(22) PCT Filed: Sep. 6, 2011

(86) PCT No.: PCT/KR2011/006582
§ 371 (c)(1),
(2), (4) Date: Feb. 26, 2014

(87) PCT Pub. No.: WO2013/032052
PCT Pub. Date: Mar. 7, 2013

(65) Prior Publication Data
US 2014/0370600 A1 Dec. 18, 2014

(30) Foreign Application Priority Data
Aug. 31, 2011 (KR) .......................... 10-2011-0087498

(51) Int. Cl.
*C12N 5/0775* (2010.01)

(52) U.S. Cl.
CPC .......... *C12N 5/0675* (2013.01); *C12N 5/0663* (2013.01); *C12N 5/0667* (2013.01); *C12N 2500/32* (2013.01); *C12N 2500/34* (2013.01); *C12N 2500/38* (2013.01)

(58) Field of Classification Search
None
See application file for complete search history.

(56) References Cited

U.S. PATENT DOCUMENTS 5,573,937 A  11/1996 Shinmoto et al.
6,150,163 A * 11/2000 McPherson et al. ......... 435/384

FOREIGN PATENT DOCUMENTS

KR  10-1037002 B1  5/2011

OTHER PUBLICATIONS

Pal et al., "Phenotypic and functional comparison of optimum culture conditions for upscaling of bone marrow-derived mesenchymal stem cells", Journal of Tissue Engineering and regenerative Medicine, 2009, vol. 3, pp. 163-174.*
Salazar et al., "Amino Acids in the cultivation of mammalian cells", Amino Acids, 2016, vol. 48, pp. 1161-1171.*
Gang, Eun Ji et al. "In vitro mesengic potential of human umbilical cord blood-derived mesenchymal stem cells" Biochemical and Biophysical Research Communications, 321 (2004), pp. 102-108.
Hildebrandt, Cornelia et al. "Influence of cell culture media conditions on the osteogenic differentiation of cord blood-derived mesenchymal stem cells" Annals of Anatomy, 191 (2009), pp. 23-32.

* cited by examiner

*Primary Examiner* — Laura Schuberg
(74) *Attorney, Agent, or Firm* — Novick, Kim & Lee, PLLC; Jae Youn Kim

(57) ABSTRACT

Disclosed is a basic culture medium for mesenchymal stem cells, and a cell therapeutic agent cultured and differentiated using same. The basic culture medium reduces the time taken from collection to mass culturing by increasing the proliferation rate of undifferentiated mesenchymal stem cells derived from an adult tissue such as human marrow and adipose tissue, and also is capable of various differentiations into treating agents for bone-forming cells, for cartilage cells, or for fat cells.

8 Claims, 9 Drawing Sheets

[Fig. 1]
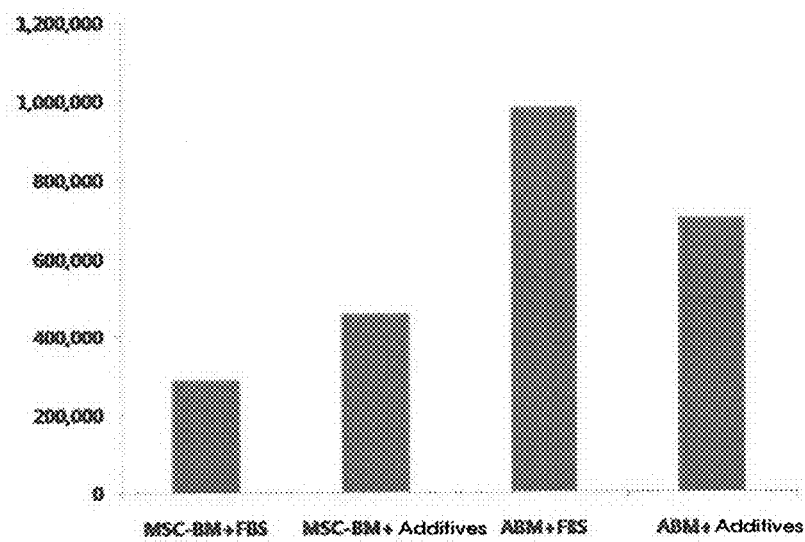
[Fig. 2]
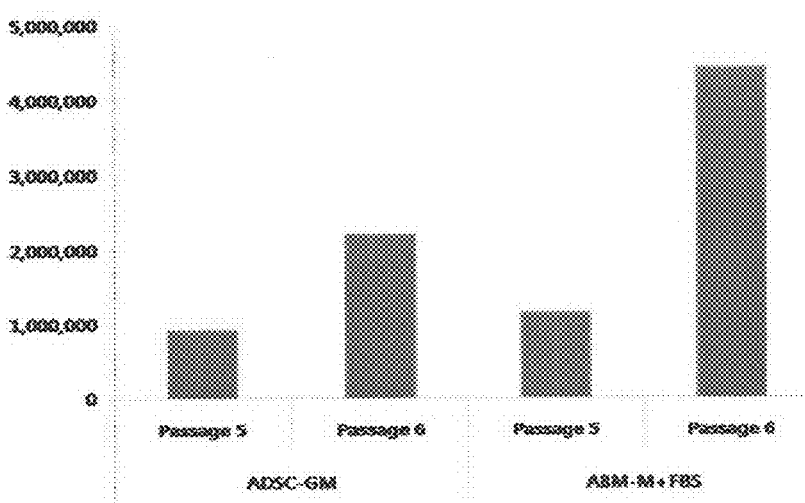

[Fig. 3]
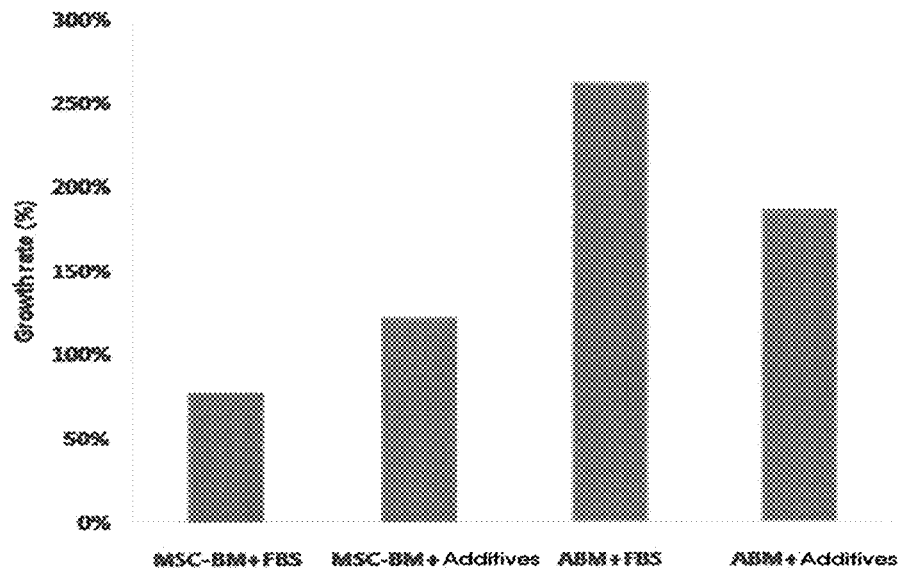
[Fig. 4]
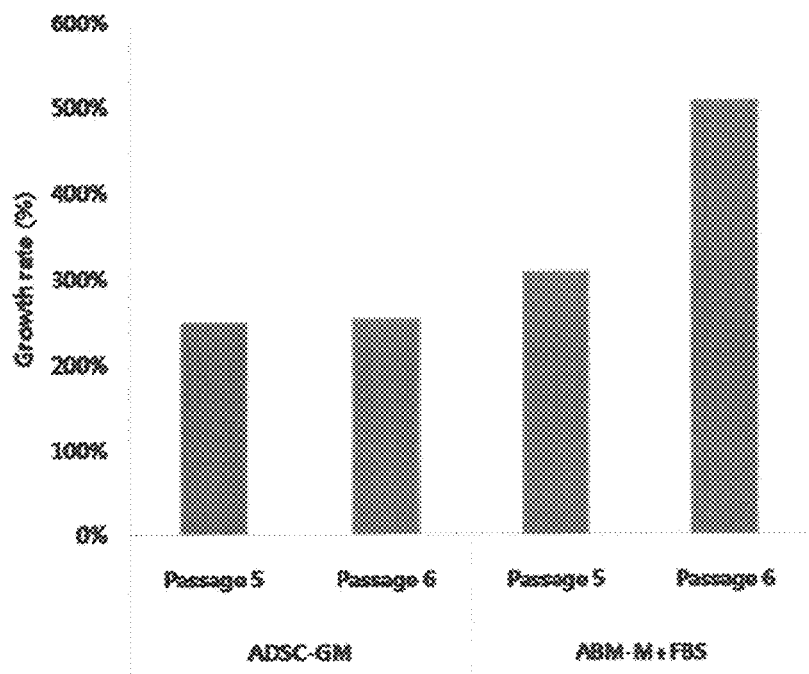

[Fig. 5]
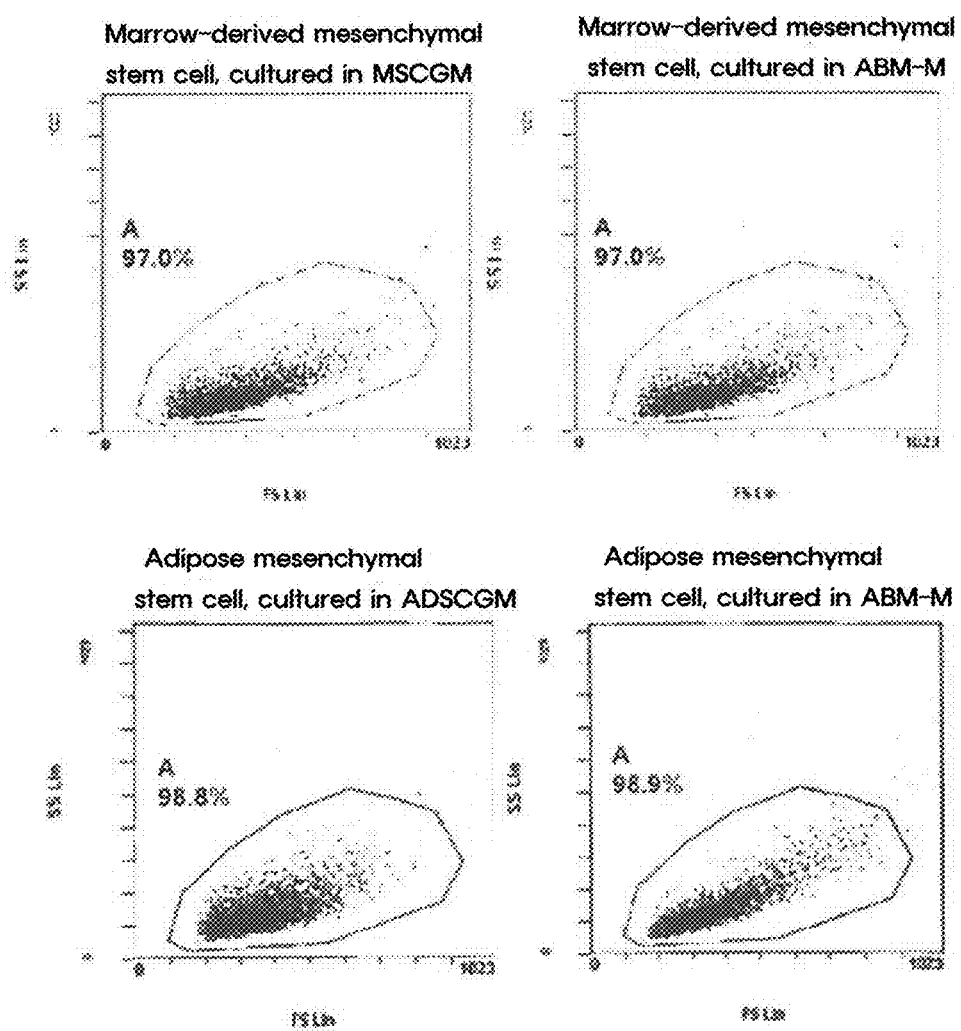

[Fig. 6]
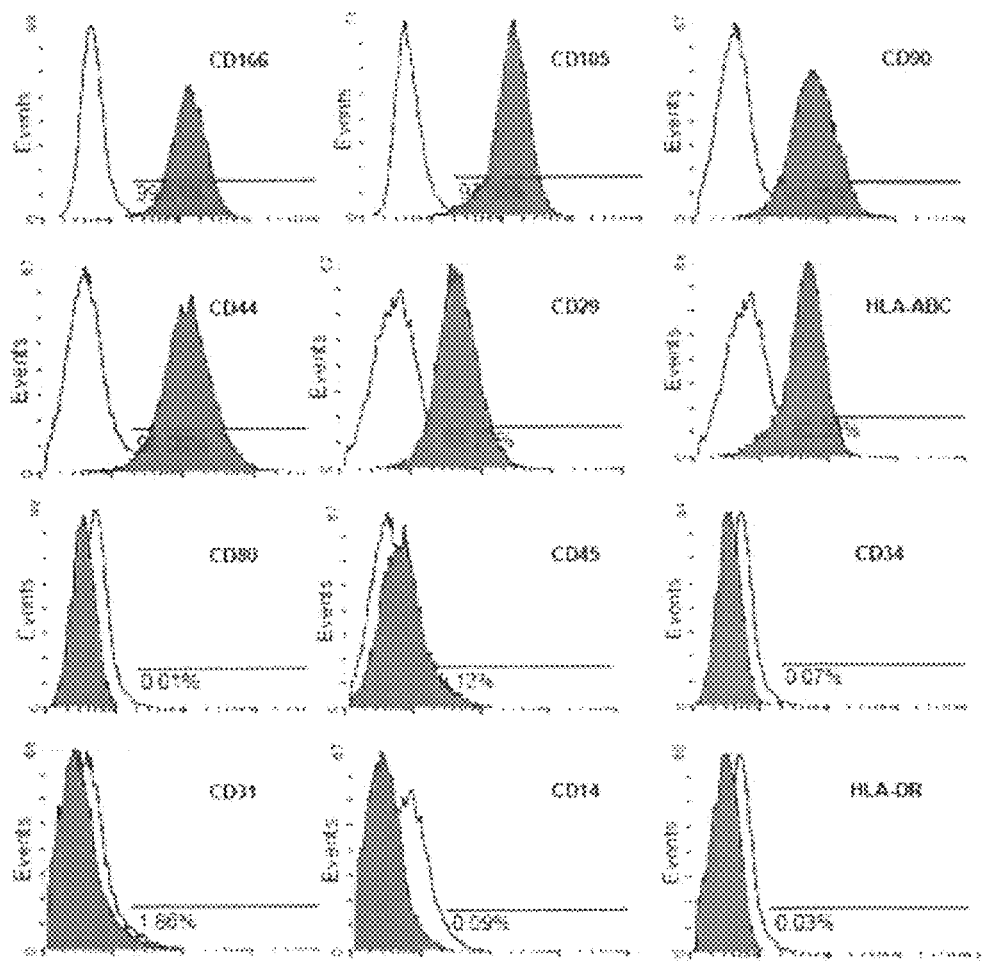

[Fig. 7]
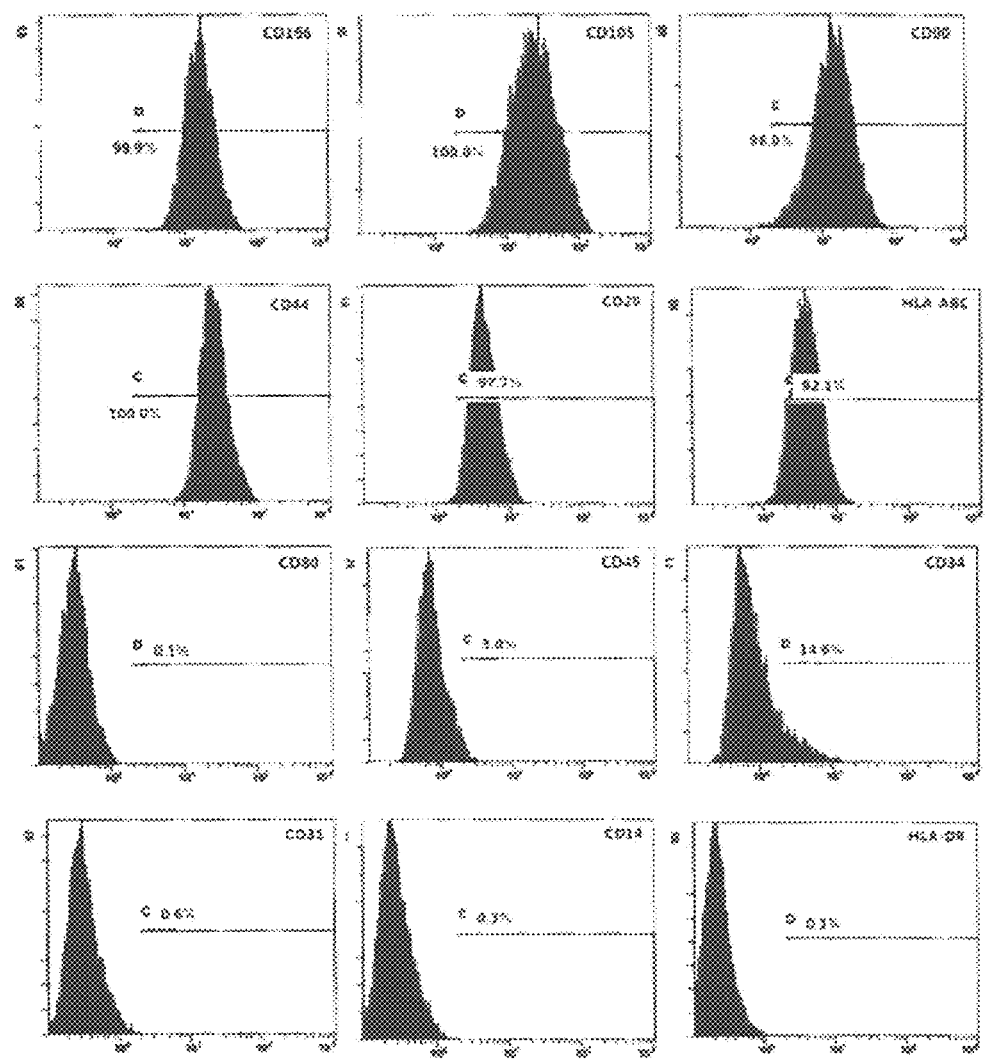

[Fig. 8]
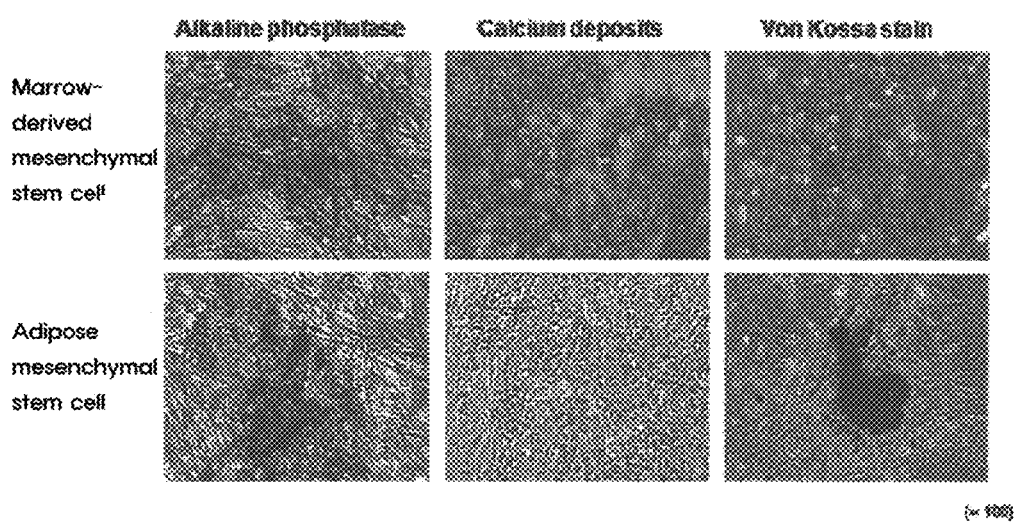

[Fig. 9]
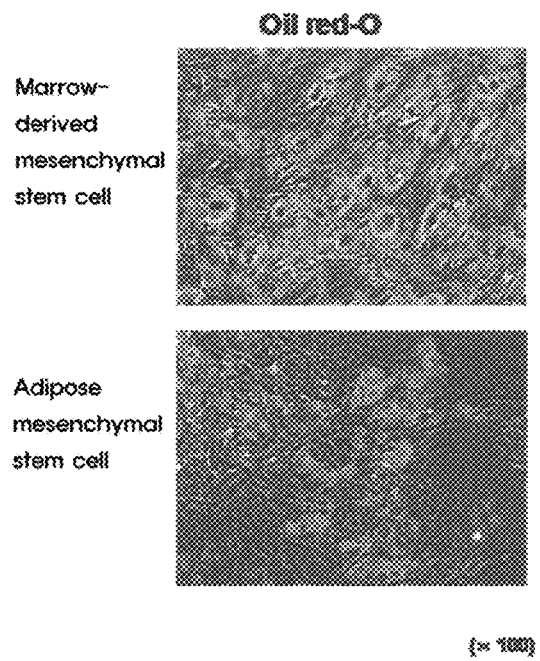
[Fig. 10]
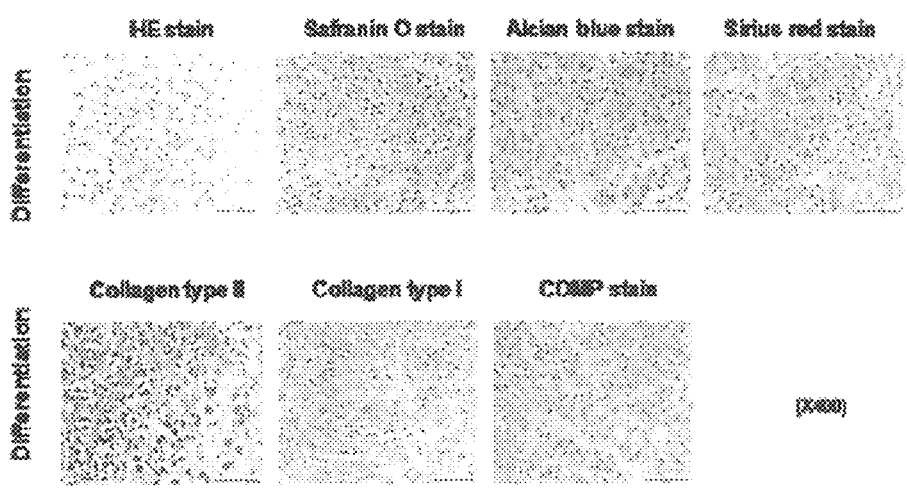

[Fig. 11]
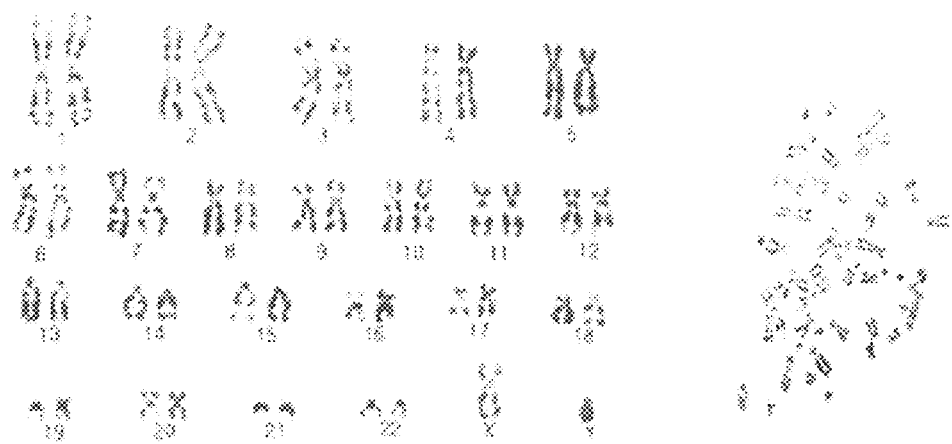
[Fig. 12]
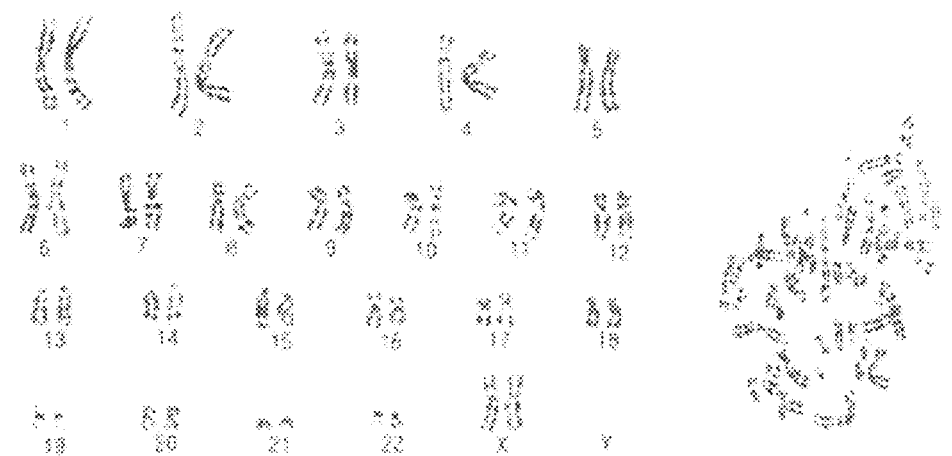

[Fig. 13]
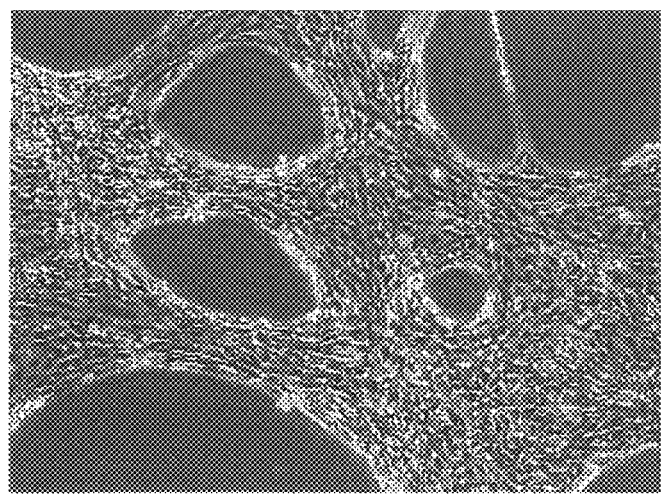

1

MESENCHYMAL STEM CELL BASIC CULTURING MEDIUM

TECHNICAL FIELD

The present invention relates to mesenchymal stem cell basic culturing medium from either marrow or fatty tissues. In particular, it is possible to cut down the time from collection to mass culturing by increasing the proliferation rate of mesenchymal stem cell, rather than culturing mesenchymal stem cell by using already-commercialized medium in the course of culturing mesenchymal stem cell in vitro (that are from either marrow or fatty tissue) By using this early-cultured mesenchymal stem cell, it is used to manufacture treatment for osteogenic cells, cartilage cells and fatty cells. Also, it includes the method of preparing multi-differentiating mesenchymal stem cell basic medium, and a way of making mesenchymal stem cell basic culturing medium and cellular therapy product that comes from its culturing/differentiation.

BACKGROUND ART

In particular, in the field of regenerative medicine using tissue engineering, the use of stem cell technology is becoming a new territory for intractable disease treatment. Accordingly, stem cell research is getting more attention. Stem cells are recognized as a problem solver not only for curing disease but also for repairing damaged tissues.

Stem cell differentiates into particular cells under an appropriate condition, by having replicative ability when it is still undifferentiated. Stem cell can be classified into Embryonic Stem Cell and Adult Stem Cell, depending on its origin. Human embryonic stem cell is acquired from an embryo that can grow to a human being. Therefore, it has an excellent cellular proliferation and differentiation ability, but is tied with life ethics. Adult stem cell is limited with differentiation ability, compared with embryonic stem cell. However, it is developed into a stem cell by taking from cells inhuman organs such as marrow, blood, brain, skin, etc. Therefore, it has less life ethics issues.

Mesenchymal Stem Cell is separated from adult marrow at first (Y. Jiang et al., Nature, 418:41, 2002). After that, it is confirmed that there found mesenchymal stem cell just like marrow, from skin, blood, muscle, brain tissues (J. G. Toma et. al., nat. Cell Biol., 3:778, 2001:M, Sampaloesi et al., Science, 301:487, 2003: Y. Jiang et al., Hematol., 30:896, 2002). Also, it is found that Adipose-derived Stem Cell that is acquired from fatty cell has the same differentiation potency like marrow (B. Cousin et al., BBRC., 301:1016, 2003).

The method of separating mesenchymal stem cell from human marrow and the method of separating mesenchymal stem cell from fatty cells are explained in Pittenger et al., (Science 284:143, 1997) and van et al., (J. Clin, Invest., 58:699, 1976). These literatures employ alpha-MEM, DMEM medium and 10-20% of small fetal serum for culturing cells.

However, there rarely exists any mesenchymal stem cell in adult cell (such as marrow, fatty tissue, etc.). In addition, these cells have low proliferation rate when they are undifferentiated. If undifferentiated, it is difficult to keep it for a long term. Therefore, if there is no screened medium, it is known to be difficult to multiply/culture/preserve in vitro.

The composition of mammal's cell culture medium consists of about 50 different kinds. They are classified into the followings: 1) a part that is used for cellular biosynthesis, 2) a part that is used for biological energy metabolism, 3) a part that is used either to act as a catalyst for various metabolisms or to adjust intracellular physiological phenomena. That is, the medium that is used for cellular culturing consists of composition of isotonic solution and buffer solution, nutrients (that include sources of energy such as amino acid, vitamins, inorganic base, etc.), and various types of supplements.

Depending on the cellular type, it provides hormones, growth factor, fat, vitamins, and suppresses the activation of protein breakdown enzyme, by providing 5-20% of blood serum. Then it promotes the growth and revitalization of mammal cells, by acting as a pH adjusting buffer. The composition of medium to culture mammal cells varies depending not only on concentration but also on the type of medium. With this method, M119 medium is made and therefore primary chick is cultured (Morgan, et al., 1950), based on body fluid composition in 1950's.

For the type of culturing medium, there are media that are used in common and simple for culturing cells, as shown in Minimal essential medium (MEM) (Eagle, 1955) and Dulbecco's modification of Eagle's medium (DMEM) (Dulbecco, et al., 1959). Just like Isocove's modification of DMEM (IMDM), Ham's F-12 (Ham, 1965) and Connaught Medical Research Laboratories (CMRL)-1666, it is possible to classify into media with more being complex and with more various components.

The growth curve of mammal cells has the lag phase of 2-3 days. The concentration of living cells significantly decreases from the end of lapse period due to the accumulation of lactate (the end product of glucose) and ammonium (the end product of glutamine metabolism). The main metabolic pathway of mammal cell is used as the main source of carbon and energy of glucose and glutamine. Once glucose is metabolized by mammal cell, it becomes Pyrubic Acid through glycosis. Also, it synthesizes hexane by making pentose by Pentose phosphate pathway. Pyrubic acid that is made through glycosis is disintegrated into $CO_2$, $H_2O$, lactate or fatty acid with TCA circuit among those carbon source that are used in cellular metabolism for mammals, apart of Glutamin becomes Glutamate during metabolism process. Glutamate enters into TCA circuit, and makes a Carbon Skeleton for the synthesis of other amino acids. Main istes of mammals are lactate and ammonia. However, the discharge of alanine is also significant. Lactate and ammonia change the pH of inside of cells and lysosome, such that they can be poisonous to cells. Likewise, the type of medium for culturing should be different, because they are different in physiological mechanism and nutrient requirement depending on the type of cultured cells.

Therefore, in order to proliferate/culture adult cell derived (marrow, fatty cells, etc.) undifferentiated mesenchymal stem cell, the condition of medium should vary depending on the growth condition of undifferentiated mesenchymal stem cell.

There have been a number of researches conducted on culturing medium in vitro that multiplies/cultures undifferentiated mesenchymal stem cell.

Patent Literature 1 (a method of mass production of growth factor using mesenchymal stem cell) is based on DMEM. Adding Ham's F-12 will accelerate the differentiation of growth factor from mesenchymal stem cell. Accordingly, it describes about serum-free medium that manipulates to synthesize significant amount of human growth factor. However, this is to mass produce basic fibroblast growth factor, venular endothelial cell growth factor or human transforming growth factor-beta, rather than the proliferation of mesenchymal stem cell in a basic medium that is mixed with DMEM and Ham's F-12.

Patent Literature 2 (medium composition that is required for cord blood-derived mesenchymal stem cell that includes soybean protein hydrolysate) is a technology to add soybean protein hydrolysate to hypoglycemosis DMEM (including fetal bovine serum), in order to reduce the amount of fetal bovine serum.

Patent Literature 3 (a method of manufacturing papilla tissue using mesenchymal stem cell) and Patent Literature 4 (a method of manufacturing papilla tissue using mesenchymal stem cell) are technologies to induce differentiation into papilla tissues, after culturing mesenchymal cells in DMEM medium, DMEM/F-12, F-12, McCoy's 5A, RPMI 1640 medium, Williams's medium E, or IMDM (Iscove's Modified Dulbecco's Modification). This relates to medium added with hydrocortisone, insulin, Transferrin and Sodium selenite in commercialized basic cell culturing medium.

Patent Literature 5 (mesenchymal stem cell culturing medium & a method of culturing mesenchymal stem cell using it) is a technology to culture by adding insulin, hydrocortisone, EGF, LIF, GM-CSF, etc. based on mixed medium (that is added with nutrient mixture) in commercialized medium. This is a technology to mix nutrient mixture in already-commercialized culturing medium.

Patent Literature 6 (adipose pluripotent stem cell & a cellular therapy product that contains it) is based on DMEM medium. It is about technology to multiply mesenchymal stem cell by adding Keratinocyte-SFM medium (that is also added with NAC, rEGF, BPE, insulin, etc.). Its basic cell culturing medium is DMEM medium.

Patent Literature 7 (culture of adult stem cell or its fraction, composition of pharmaceutical treatment and cancer treatment) and Patent Literature 8 (separated pluripotency adult stem cell and its separation/culturing) are technologies to culture mesenchymal stem cell by using DMEM/Ham's F-12 mixed medium, DMEM medium and DMEM/F-12.

These conventional technologies are limited to those that culture previously commercialized medium by adding additives such as growth factor.

However, our patent (Patent Literature 9) (a method of special culturing of cartilage cells for early culturing of cartilage cells) is the one to develop culture medium without adding additives such as growth factor, etc. By using early-cultured medium (ABM-C) of Patent Literature 9, the mesenchymal stem cell (one that is separated from adult cells such as marrow and fat) is cultured. However, there found morphological anomaly during cell culturing as shown in FIG. 13. Also, without adhesiveness, it floats on cell culturing medium. Therefore, mesenchymal stem cell does not proliferate, the one that multiplies being attached to in vitro.

PRECEDING TECHNOLOGY LITERATURE

Patent Literature (Patent Literature 1): Republic of Korea Patent Registration Number 10-0899329
(Patent Literature 2) Republic of Korea Open Patent Number 10-2009-0090850
(Patent Literature 3): Republic of Korea Patent Registration Number 10-1022032
(Patent Literature 4) Republic of Korea Open Patent Number 10-2010-0110905
(Patent Literature 5): Republic of Korea Patent Registration Number 10-0908481
(Patent Literature 6): Republic of Korea Patent Registration Number 10-0679642
(Patent Literature 7) Republic of Korea Open Patent Number 10-2009-0121541
(Patent Literature 8) Republic of Korea Open Patent Number 10-2006-0010847
(Patent Literature 9): Republic of Korea Patent Registration Number 10-1037002

DISCLOSURE

Technical Problem

Accordingly, the present invention has been made keeping in mind the above problems occurring in the prior art, and an object of the present invention is to provide mesenchymal stem cell basic culturing basin that can culture/multiply undifferentiated mesenchymal stem cell (from adult cells such as marrow, fatty cell, etc.) in a large scale at a very fast growth speed.

Another object of the present invention is to provide cellular therapy product that contains undifferentiated mesenchymal stem cell by differentiating undifferentiated mesenchymal stem cell (from in vitro adult cell) into osteogenic cells, cartilage cells and fatty cells, using mesenchymal stem cell basic culturing medium.

The aforementioned object of the present invention is to analyze the types of commercialized culturing medium components, to combine two or more culturing media, and to prepare various types of basic culturing media. Among those basic culturing media, the multiplication rate of mesenchymal stem cell is analyzed in a complete medium that contains 10-20% of fetal bovine serum. Accordingly, the end result is to use and prepare a procedure to make basic media-mesenchymal stem cell. This method includes a screening step of preparing a basic culturing medium, appropriate to early-culturing of mesenchymal stem cell.

In addition, the object of the present invention is to compare 1) a basic medium that is mixed with a 1:1:1 ratio of DMEM high glucose (a commercialized culturing medium), RPMI-1640 and Ham's F-12 with 2) each of DMEM high glucose, RPMI-1640 and Ham's F-12 medium. The basic component includes the components of DMEM high glucose medium. In case of repeatedly used component in each medium, a higher concentration is selected. If it is not included in DMEM high glucose medium, it should be included in DMEM high glucose medium. If it is a component that is not included in any medium, it should be included in DMEM high glucose medium. By selecting a component among those with the same source of supply, if a component is repeatedly used, a higher concentration is selected. If it is not included in DMEM high glucose medium, it should be included in DMEM high glucose medium. Therefore, the object is to create a mesenchymal stem cell basic culturing medium that made ABM-M (Advanced Basic Media-Mesenchymal stem cell) medium.

Technical Solution

For a mesenchymal stem cell basic culturing medium, those components that are a part of DMEM high glucose medium are as follows. For amino acids, there are L-Alanine, L-Asparagine Anhydrous, L-Aspartic acid, L-Glutamic acid, L-Hydroxy-L-proline, and L-proline. For Inorganic Salts, there are Cupric Sulfate Pentahydrate, Ferrous Sulfate Heptahydrate, Sodium Phosphate Dibasic Anhydrous, and Zinc Sulfate Heptahydrate. For Vitamins, there are D-Biotin, P-Aminobenzoic Acid (PABA), and Vitamin B12. For other components, there are Hypoxanithine, L-Glutathione Reduced, Linoleic acid, Putrescine+2HCL, Thioctic Acid, and Thymidine.

For mesenchymal stem cell basic culturing medium of the present invention, ABM-M medium includes one or more from serum of embryo, calf, horse, or human, L-Glutamine, antibiotics and antifungal.

As for mesenchymal stem cell basic culturing medium of the present invention, ABM-M medium contains 10-20% of fetal bovine serum and 2-4 mM of L-glutamine in addition.

For basic culturing media of mesenchymal stem cell, there are components that should be selected from the same source of supply. For amino acids, there are: L-Arginine Monobydrochloride, L-Aspartic Acid, L-Cystine Dihydrochloride, L-Histidine Monobydrochloride Monohydrate. For Inorganic Salts, there are Calcium Chloride Dihydrate, Ferrous Sulfate, Heptahydrate, Magnesium Sulfate Anhydrous, and Sodium Phosphate Dibasic Anhydrous. For Vitamins, there is Pyridoxal Hydrochloride.

For basic media mesenchymal stem cell of the present invention, ABM-M medium manifests over 80% of positive surface marker for CD166, CD105, CD90, CD44, CD29, CD73 and HLA-ABC. The positive surface marker for CD44, CD105, CD90, CD73, and CD166 is manifested over 95%. The negative surface marker for CD14, CD31, CD34, CD45, CD80 and HLA-DR is manifested less than 5%.

Also, the object of the present invention is as follows. A mesenchymal stem cell is cultured in ABM-M (Advanced Basic Media-Mesenchymal stem cell). After that, it is cultured/differentiated in alpha-MEM medium that includes fetal bovine serum, Dexamethasone, beta-Glycerophosphate and Ascorbic acid. The cellular therapy product for segmental bone defects is one that differentiates into osteogenic cells.

The following is another object of the present invention. A mesenchymal stem cell is cultured in ABM-M (Advanced Basic Media-Mesenchymal stem cell). Then it is cultured/differentiated in DMEM low glucose medium that includes Dexamethasone, Ascorbic acid and Sodium pyruvate, TFG-beta, BMP-2. This is later differentiated into cartilage cells. The end result is a cellular therapy product for osteoarthritis with the abovementioned characteristics. Another object of the present invention is as follows: Mesenchymal stem cells are cultured in ABM-M (Advanced Basic Media-Mesenchymal stem cell) medium. Then, it is cultured/differentiated in alpha-MEM medium that includes fetal bovine serum, Dexamethasone, Indomethacin, and Insulin. This is later differentiated into fatty cells. The end result is to develop a cellular therapy product for fatty tissue formulation with the abovementioned characteristics.

Advantageous Effects

As described above, according to the present invention, it is possible to multiply differentiated mesenchymal stem cell (an adult stem cell) at a very fast speed with the advanced basic media-mesenchymal stem cell of the present invention. It is possible to maintain cellular karyotype even after multiplying for long term over a month. It is also possible to use it as a cellular therapy product by differentiating into osteogenic cells, cartilage cells and fatty cells.

DESCRIPTION OF DRAWINGS

FIG. 1 shows a medium of marrow derived mesenchymal stem cell that contains MSC-BM (control group), additives and 10% of fetal bovine serum, and also shows the procedure of inoculating the concentration of 375,000 cells in T75 flask that includes ABM-M medium, additives and 10% of fetal bovine serum, in which FIG. 1 is a graph showing the growth of mesenchymal stem cell after 10 days of culturing.

FIG. 2 is a view showing a stem cell cultured for 7 days after inoculating adipose mesenchymal stem cell with the concentration of 375,000 cells in T75 flask that contains ADSCM (control group), ABM-M medium, 10% of fetal bovine serum and then it is subcultured with the growth of mesenchymal stem cell, inoculated with the concentration of 875,000 cells in T175 flask, and cultured for 7 days, in which FIG. 2 is a graph showing the growth of mesenchymal stem cell, and marrow derived mesenchymal stem cell uses additives and 10% of fetal bovine serum in MSC-BM (control group) & also with additives and 10% of fetal bovine serum in ABM-M medium.

FIG. 3 is a graph showing the proliferation rate of mesenchymal stem cell.

FIG. 4 is a graph showing the growth of mesenchymal stem cell for respective subculturing, which are multiplied in a medium that contains ADSCGM (control group), ABM-M medium, and 10% of fetal bovine serum.

FIG. 5 shows a graph (SS; granular content within cell, FS; cell size) of cellular size and a change of phenotype by carrying out flow cytometer on adipose mesenchymal stem cell, or marrow that is cultured in culturing medium that contains 10% of fetal bovine serum and 2 mM L-glutamine in ABM-M, MSCGM medium (control group), ADSCGM medium or adipose mesenchymal stem cell.

FIG. 6 is a graph showing histogram of immunological cellular analysis for marrow derived mesenchymal stem cell, which is cultured in a medium that contains 10% of fetal bovine serum, 2 mM L-glutamine in ABM-M medium.

FIG. 7 is a graph showing histogram of cellular characteristic analysis for adipose mesenchymal stem cell, which is cultured in a medium that contains 10% of fetal bovine serum, 2 mM L-glutamine in ABM-M medium.

FIG. 8 is an ALPase and von Kossa dyeing picture after re-culturing/differentiating for 2-3 weeks in osteogenic cells (in alpha-MEM medium that includes 10% of fetal bovine serum, 10 mM beta-glycerol phosphate, 50 uM ascorbic acid, $10(-7)$M dexamethasone), after culturing marrow-derived/adipose mesenchymal stem cells in a medium that contains 10% of fetal bovine serum and 2 mM of L-glutamine in ABM-M medium.

FIG. 9 is an oil Red-O dyeing picture after re-culturing/differentiating for 2 weeks in adipose differentiating medium (alpha-MEM medium that contains 10% of fetal bovine serum, $10(-7)$M dexamethasone, 100 uM indomethacin and 10 ug/mL insulin), after culturing marrow-derived/adipose mesenchymal stem cell that is cultured in a medium containing 10% of fetal bovine serum, 2 mM L-glutamine in ABM-M medium.

FIG. 10 shows a procedure where cellular clump is made by centrifugation about 5 $10(5)$ cells for 5 minutes at 300 g, in order to induce differentiation into cartilage cells, after culturing marrow-derived mesenchymal stem cell that is cultured in a medium containing 10% of fetal bovine serum and 2 mM L-glutamine in ABM-M medium, cartilage tissues is re-cultured/differentiated for 3 weeks in DMEM high glucose medium that contains $10(-7)$ M dexamethasone, 50 uM ascorbic acid, 1 nM sodium pyruvate, 10 ng/mL TGF beta, 100 ng/mL BMP 2, and it is put through paraffin embedding process, to manufacture serial section in which FIG. 10 shows dyeing pictures of H/E dyeing, safranin O dyeing, alcian blue dyeing, Sirius red dyeing, COMP dyeing, collagen type II, and I dyeing.

FIG. 11 is a picture that analyzed karyotype after subculturing marrow-derived mesenchymal stem cell 10 times (that is cultured in a medium that contains 10% of fetal bovine serum and 2 mM L-glutamine) in ABM-M medium.

FIG. 12 is a picture that analyzed karyotype after subculturing adipose mesenchymal stem cell 10 times (that is cultured in a medium that contains 10% of fetal bovine serum and 2 mM L-glutamine) in ABM-M medium.

FIG. 13 is a picture that shows abnormality and lack of adhesiveness of mesenchymal stem cell during cellular culturing process in the previous ABM-C medium.

BEST MODE

Mode for Invention

The present invention provides an advanced basic adult cell derived mesenchymal stem cell medium, which is from adult cells such as marrow, fat, etc. The basic mesenchymal stem cell medium for the present invention analyzes the type of component in commercialized medium. After that, in combination of media with 2 or more types, there is a step of preparing various types of rear basic culturing media. For the candidates of basic culturing media, complete medium is analyzed for the proliferation rate of mesenchymal stem cell, which includes 10-20% of fetal bovine serum. This is prepared by including a step of screening basic culturing medium, which can be appropriate to mesenchymal stem cell.

By using basic media mesenchymal stem cell that is made for the present invention, it is analyzed if the accelerated-early-cultured mesenchymal stem cell shows immunological cellular characteristics. Also its differentiation potency is analyzed if they are differentiated into osteogenic cells, cartilage cells and fatty cells. Cellular karyotype is analyzed to see if it can be cultured for long term without making mutation with chromosomal anomaly. Accordingly, it will be verified if it can be used as cellular therapy product for treatment of segmental bone defects, osteoarthritis, and also that of fatty cells.

In order to verify if it can be used as cellular therapy product by using the advanced basic media-mesenchymal stem cell, it is desirable to verify in the following procedure to analyze immunological cellular characteristics, differentiation potency and cellular karyotype. First, a step of analyzing immunological cellular characteristics of mesenchymal stem cell that is cultured in screened medium: a step of analyzing differentiation potency of mesenchymal stem cell that is cultured by creating screened medium: a step of analyzing cellular karyotype to see if it is possible to culture mesenchymal stem cell (that is prepared with screened medium) for a long term.

The followings are more detailed explanation on the present invention.

The ABM-M (Advanced Basic Media-Mesenchymal stem cell) of the present invention is prepared with a basic medium that is mixed in 1:1:1 ratio of DMEM high glucose, RPMI-1640 and Ham's F-12, which is a commercialized culturing medium. With DMEM high glucose as a basic component, the abovementioned basic medium is compared with respective medium of DMEM high glucose, RPMI-1640 and Ham's F-12. Then, a higher concentration is selected for those components that are used repeatedly in other media. If it is not included in DMEM high glucose medium, it is included in DMEM high glucose (refer to Note (1) of Table 1). Those components that are included in only one medium keep the same concentration. If they are not included in DMEM high glucose medium, they are included to DMEM high glucose medium (Note (2) of Table 1). Those that use the same source of supply among respective medium components, one component is chosen. If a component is repeatedly used in other media, a higher concentration is selected. If it is a component that is not included in DMEM high glucose medium, it is included in DMEM high glucose medium (Note (3) of Table 1). As a result, Table 1 is prepared as shown below.

TABLE 1

Preparation of Commercialized Medium and Preparation of ABM-M Medium

| Components (mg/L) | DMEM | RPMI | F-12 | ABM-M | Note |
|---|---|---|---|---|---|
| Amino Acids | | | | | |
| Glycine | 30 | 10 | 7.51 | 30 | ① |
| L-Alanine | | | 9 | 9 | ②, inclusion inclusion |
| L-Arginine Free Base | | 200 | | | ③ |
| L-Arginine Monohydrochloride | 84 | | 211 | 211 | |
| L-Asparagine Anhydrous | | 50 | | 50 | ③, inclusion |
| L-Asparagine Monohydrate | | | 15.01 | | |
| L-Aspartic acid | | 20 | 13.3 | 20 | ①, inclusion |
| L-Cysteine Monohydrochloride Monohydrate | | | 35 | | ③ |
| L-Cystine Dihydrochloride | 62.6 | 65.2 | | 62.6 | |
| L-glutamic Acid | | 20 | 14.7 | 20 | ①, inclusion |
| L-Glutamine | 584 | 300 | 146 | 584 | ① |
| L-Histidine | | 15 | | | ③ |
| L-Histidine Monohydrochloride | 42 | | 20.96 | 42 | |
| L-Hydroxy-L-Proline | | 20 | | 20 | ②, inclusion |
| L-Isolcucine | 105 | 50 | 3.94 | 105 | ① |
| L-Leucine | 105 | 50 | 13.1 | 105 | ① |
| L-Lysine Monohydrochloride | 146 | 40 | 36.5 | 146 | ① |
| L-Methionine | 30 | 15 | 4.48 | 30 | ① |
| L-Phenylalanine | 66 | 15 | 4.96 | 66 | ① |
| L-Proline | | 20 | 34.5 | 34.5 | ①, inclusion |
| L-Serine | 42 | 30 | 10.5 | 42 | ① |
| L-Threonine | 95 | 20 | 11.9 | 95 | ① |

TABLE 1-continued

Preparation of Commercialized Medium and Preparation of ABM-M Medium

| Components (mg/L) | DMEM | RPMI | F-12 | ABM-M | Note |
|---|---|---|---|---|---|
| L-Tryptophan | 16 | 5 | 2.04 | 16 | ① |
| L-Tyrosine Disodium Salt Dihydrate | 103.79 | 28.83 | 7.78 | 103.79 | ① |
| L-Valine | 94 | 20 | 11.7 | 94 | ① |
| Inorganic Salts | | | | | |
| Calcium Chloride Dihydrate | 265 | | 44.1 | 265 | ③ |
| Calcium Nitrate | | 100 | | | |
| Cupric Sulfate Pentahydrate | | | 0.0025 | 0.0025 | ②, inclusion |
| Ferric Nitrate Nonahydrate | 0.1 | | | | ③, inclusion |
| Ferrous Sulfate Heptahydrate | | | 0.834 | 0.834 | |
| Magnesium Chloride Hexahydrate | | | 123 | | ③ |
| Magnesium Sulfate Anhydrous | 97.67 | 48.84 | | 97.67 | |
| Potassium Chloride | 400 | 400 | 224 | 400 | ① |
| Sodium Chloride | 6,400 | 5,300 | 7,599 | 6,400 | ① |
| Sodium Phosphate Dibasic Anhydrous | | 800 | 142.04 | 142.04 | ③, inclusion |
| Sodium Phosphate Monobasic Anhydrous | 109 | | | | |
| Zinc Sulfate Heptahydrate | | | 0.863 | 0.863 | ②, inclusion |
| Vitamins | | | | | |
| Ascorbic Acid Phosphate | 50 | 50 | 50 | 50 | ① |
| Choline Chloride | 4 | 3 | 13.96 | 13.96 | ① |
| D-Biotin | | 0.2 | 0.0073 | 0.2 | ①, inclusion |
| D-Ca Pantothenate | 4 | 0.25 | 0.48 | 4 | ① |
| Folic Acid | 4 | 1 | 1.32 | 4 | ① |
| Myo-Inositol | 7.2 | 35 | 18 | 35 | ① |
| Nicotinamide (Nicotinic acid amide) | 4 | 1 | 0.037 | 4 | ① |
| P-Aminobenzoic Acid (PABA) | | 1 | | 1 | ②, inclusion |
| Pyridoxal Hydrochloride | 4 | | | 4 | ③ |
| Pyridoxine Hydrochloride | | 1 | 0.062 | | |
| Riboflavin | 0.4 | 0.2 | 0.038 | 0.4 | ① |
| Thiamine Hydrochloride | 4 | 1 | 0.34 | 4 | ① |
| Vitamin B12 | | 0.005 | 1.36 | 1.36 | ①, inclusion |
| Other Components | | | | | |
| D-glucose Anhydrous | 4,500 | 2,000 | 1,802 | 4,500 | ① |
| Hypoxanthine | | | 4.08 | 4.08 | ②, inclusion |
| L-Glutathione Reduced | | 1 | | 1 | ②, inclusion |
| Linoleic acid | | | 0.084 | 0.084 | ②, inclusion |
| Phenol Red Sodium Salt | 15.9 | 5.3 | 1.3 | 15.9 | ① |
| Putrescine + 2HCL | | | 0.161 | 0.161 | ②, inclusion |
| Sodium Pyruvate | 110 | | 110 | 110 | ① |
| Thioctic Acid | | | 0.21 | 0.21 | ②, inclusion |
| Thymidine | | | 0.73 | 0.73 | ②, inclusion |

As mentioned in Notes of Table 1, the followings are those that are added to DMEM high glucose medium (basic component of ABM-M medium). For amino acids, there are L-Alanine, L-Asparagine Anhydrous, L-Aspartic acid, L-Glutamic acid, L-Hydroxy-L-proline, and L-Proline. For inorganic salts, there are Cupric Sulfate Pentahydrate, Ferrous Sulfate Heptahydrate, Sodium Phosphate Dibasic Anhydrous, and Zinc Sulfate Heptahydrate. For vitamins, there are D-Biotin, P-Aminobenzoic Acid (PABA), and Vitamin B12. For other components, there are Hypoxanthine, L-Glutathione Reduced, Linoleic acid, Putrescine+ 2HCL, Thioctic Acid, and Thymindine.

The following is the description on Note of Table 1 that shows the composition of ABM-M (Advanced Basic Media-Mesenchymal stem cell) medium, which is the basic culturing medium of mesenchymal stem cell.

(1) For any component that is repeatedly used among media, use a higher concentration. If it is not included in DMEM high glucose medium, those that are included in DMEM high glucose are listed in Note (1) of Table 1.

The mesenchymal stem cell (that is originated from adult stem cell in ABM-C medium with DMEM, RPMI-1640: refer to Patent Document No. 9) is cultured. As a result, there found a lack of adhesivity and some abnormality in cellular shape. Therefore, in order to reinforce these, some component are added that are particularly relevant to proliferation rate and cellular synthesis.

Glycine, L-Glutamine, L-Isoleucine, L-Leucine, L-Lysine, L-Methionine, L-Phenylalanine, L-Serine, L-Threonine, L-Tryptophan, L-Tyrosine, and L-Valine are major amino acids that are used for protein synthesis. By selecting a higher concentration, it helps promoting protein synthesis and cellular proliferation.

Potassium Chloride and Sodium Chloride (inorganic salts) are concerned with intracellular osmotic pressure. Therefore, a component on the higher end is selected to keep an appropriate osmotic pressure.

The following vitamins are anti-oxidants: Ascorbic Acid Phosphate, Choline Chloride, D-Biotin (included in DMEM high glucose medium), D-Ca Pantothenate, Folic Acid, Myo-Inositol, Nicotinamide, Riboflavin, Thiamine Hydrochloride, and Vitamin B12 (included in DMEM high glucose medium). That is to say, a higher concentration is selected to remove istes, which are generated from high cellular proliferation.

D-Glucose Anhydrous (other components) is a major source of energy. Therefore, in order to keep a higher proliferation rate, a higher concentration is selected. Sodium Pyruvate is related to intercellular synthesis, such that a higher side is selected. Phenol Red Sodium Salt is irrelevant to cellular proliferation. However, they are istes generated as cellular proliferation becomes more active. Phenol Red's color changes from red to yellow. Due to a high proliferation rate, a higher concentration is selected to measure the amount of discharged istes in time.

Proline is a main component of collagen, and also is a major component of compound synthesis of cells. In order to increase the synthesis of collagen within highly proliferating mesenchymal stem cell, it is included into DMEM high glucose medium.

Aspartic acid is included in most of proteins, and also is connected to citric acid cycle. It is an amino group supplier for purine base. Therefore, the major supplier of cell DNA synthesis with high proliferation rate is purine and pirimidine base, such that they are included into DMEM high glucose medium.

L glutamic acid is an amino acid that is significant to cell metabolism. Therefore, it is also included into DMEM high glucose medium for active cell proliferation.

Those components that are included in only one medium keep the same concentration. If they are not included in DMEM high glucose medium, those that are included to DMEM high glucose medium are Note (2) of Table 1.

There is a lack of cell adhesiveness, in case of mesenchymal stem cell in ABM-C medium (is made up of DMEM and RPMI-1640) that increased proliferation rate. In order to reinforce this, the synthesis of intracellular collagen, those that are not in DMEM high glucose medium are included, as a way of removing istes from increased synthesis.

L-Alanine (an amino acid) is an amino acid that is related to cell immunity and synthesis, and therefore is included to increase proliferation of mesenchymal stem cell. L-Hydroxy-L-Proline (an amino acid), Thioetic Acid & Linoleic Acid (other components) and P-Aminobenzoic Acid (PABA) (a vitamin) are components of intracellular collagen, which increase the synthesis of intracellular collagens and also enhance the adhesiveness. Therefore, they are included in DMEM high glucose medium.

Cupric Sulfate Pentahydrate and Zinc Sulfate Heptahydrate (Inorganic Salts) and Glutathione Reduced (Other components) are anti-oxidants. They increase the discharge of various intracellular (one that shows a high proliferation rate) istes. Therefore, they are included in DMEM high glucose medium to have higher cell proliferation rate.

Other components such as Thymidine, Putrescine+2HCL, and Hypoxanthine DNA are components that are involved in DNA synthesis. To increase cell proliferation rate, DNA synthesis is a prerequisite. Therefore, they are included in DMEM high glucose medium.

(3) Those that use the same source of supply among respective medium components choose one component. If the selected component is one that is used again in different medium, select a higher concentration. If it is not included in DMEM high glucose medium, those that are included in DMEM high glucose are listed in Note (3) of Table 1.

For L-Arginine, L-Asparagine, L-Cysteine/cystine, L-Histidine (amino acids), Calcium Chloride/Nitrate, Ferric Nitrate/Ferrous Sulfate, Sodium Phosphate (Inorganic Salts), and Pyridoxal Hydrochloride/Pyridoxine Hydrochloride (Vitamins), adding two or more that have the same source of supply, it may have an adverse effect on cell due to increased osmotic pressure. Therefore, for the same components, either a component with high concentration or a single source of supply is selected.

Also, in order to minimize the salts that can be produced from batch process, those with hydrate are selected among inorganic salts.

For Sodium phosphate, selecting a high concentration may increase the overall osmotic pressure in medium. This may have an adverse effect on cell, such that 142.04 mg/L is selected to maintain an appropriate osmotic pressure.

Magnesium Chloride Hexahydrate and Magnesium Sulfate Anhydrous are the source of magnesium supply, which is the major component of intracellular metabolism. Therefore, in order to decrease salts during batch process, an anhydrous (Magnesium Sulfate Anhydrous) is selected. However, it is a component that is used again, such that one with higher concentration is selected.

Due to the abovementioned reasons as shown in Table 1, L-Arginine Monohydrochloride (211 mg/L) between L-Arginine Free Base (RPMI) and L-Arginine Monohydrochloride (DMEM, F12) is selected. Also, L-Asparatic acid (20 mg/L) between L-Asparagine Monohydrate and L-Asparatic acid is selected. L-Cystine Dihydrochloride (62.6 mg/L) is selected between L-Cysteine Monomydrochloride Monohydrate, L-Cystine Dihydrochloride. L-Histidine Monohydrochloride Monomhydrate (42 mg/L) is selected between L-Histidine and L-Histidine Monohydrochloride Monohydrate.

For Inorganic Salts, Calcium Chloride Dihydrate (265 mg/L) is selected between Calcium Chloride Dihydrate and Calcium Nitrate Tetrahydrate. Ferrous Sulfate Heptahydrate (0.834 mg/L) between Ferric Nitrate Nonahydrate and Ferrous Sulfate Heptahydrate is selected. Magnesium Sulfate Anhydrous (97.67 mg/L) between Magnesium Chloride Hexahydrate and Magnesium Sulfate Anhydrous is selected. Sodium Phosphate Dibasic Anhydrous (142.05 mg/L) between Sodium Phosphate Dibasic Anhydrous and Sodium Phosphate Monobasic Anhydrous is selected.

For vitamins, Pyridoxal Hydrochloride (4 mg/L) between Pyridoxal Hydrochloride and Pyridoxine Hydrochloride is selected.

As explained above, the object of Advanced Basic Media-Mesenchymal stem cell (ABM-M) is to culture in vitro adult cell derived (marrow, fatty cell, etc.) mesenchymal stem cell. It starts with the preparation of DMEM high glucose, RPMI-1640 and Ham's F-12 media. However, the basic component is DMEM high glucose.

That is to say, the ABM-M medium is classified as an adult stem cell that is neither actively proliferating nor synthesizing. Therefore, its main component is DMEM high glucose medium with high concentration of amino acid. Also, this medium is adjusted with the concentration of components such as amino acid, inorganic salts, vitamins, etc., which may be either non-existent or ones with low concentration in DMEM high glucose.

Mesenchymal stem cell is referred to as non-differentiated cells with multipotency ability that comes from adult cells of mammal (including human being). Adjust cells include marrow, blood, brain, skin, fat, cord blood, etc.

It is possible to separate mesenchymal stem cells from the abovementioned adult cells such as marrow or fatty cells in various methods. For instance, it is possible to use a separation method with concentration radiant centrifugation by Percoll et al. (Majumdar M K et al., J. Cell Physiol, 17:57, 1998; Majka S M et al., J. Clin. Invest., 111:71, 2003) or a method of Luria et al. (Luria et al., Transfusion, 11:345, 1972) separating cells with enzymatic treatment with collagenase. These can separate all the cells that grow on the bottom of culturing flask easily.

The purpose of advanced basic media mesenchymal stem cell is to culture mesenchymal stem cell, separated from adult cells such as marrow, blood, brain, skin, cord blood, etc. If necessary, it is possible to add one or more component. It also can be added with antibiotics and antifungal agents to prevent microorganism's pollution such as fetal calf, horse/human serum and L-glutamine. More ideally, it is desirable to add 10-20% of fetal bovine serum and 2-4 mM of L-glutamine.

In order to find the proliferation rate from advanced basic media mesenchymal stem cell (ABM-M), mesenchymal stem cell is cultured in basic culturing medium for the present invention. The followings are immunological cellular characteristics of mesenchymal stem cell. A positive surface market for CD166, CD105, CD90, CD44, CD29, CD73, and HLA-ABC is manifested over 80%. In particular, the positive surface marker for CD44, CD105, CD90, CD73 and CD166 is manifested over 95%. A negative surface marker for CD31, CD34, CD45, CD80 and HLA-DR is manifested less than 5%. So, they show immunological cellular characteristics.

It also shows morphological characteristics of spindle-shape, attaching/proliferating on the surface of plastic culturing container. Also, it is proliferated disdifferentiating.

It is confirmed that the cultured mesenchymal stem cell can differentiated into osteogenic cells, cartilage cells and fatty cells, which shows that it is a multi-potency mesenchymal stem cell.

For the present invention, mesenchymal stem cell is cultured in ABM-M (Advanced Basic Media-Mesenchymal stem cell), which is followed by culturing again in alpha-MEM medium that contains fetal bovine serum, Dexamethansone, beta-Glycerophosphate, and Ascorbic acid. This provides a cell therapy product for segmental bone defects that contains mesenchymal stem cell, which can differentiate into osteogenic cells.

For the present invention, mesenchymal stem cell is cultured in ABM-M (Advanced Basic Media-Mesenchymal stem cell), which is followed by culturing again in DMEM low glucose medium that contains Dexamethansone, Ascorbic acid, Sodium pyruvate, TFG-beta, and BMP-2. This provides a cell therapy product for osteoarthritis that contains mesenchymal stem cell, which can differentiate into cartilage cells. For the present invention, mesenchymal stem cell is cultured in ABM-M (Advanced Basic Media-Mesenchymal stem cell), which is followed by culturing again in alpha-MEM medium that contains fetal bovine serum, Dexamethasone, Indomethancin, and Insulin. This provides a cell therapy product for osteoarthritis that contains mesenchymal stem cell, which can differentiate into fatty cells.

Type of Implementation

In the present invention, the proliferation of mesenchymal stem cell in Advanced Basic Media-Mesenchymal stem cell (ABM-M) is compared with other medium. More detailed explanation is given in the following practical examples, which includes the immunological cellular characteristics of mesenchymal stem cell (that is cultured in ABM-M), the differentiation potency of mesenchymal stem cell (that is cultured in ABM-M medium), and maintain cellular karyotype of mesenchymal stem cell (that is cultured in ABM-M medium).

Practical Example 1

Comparison of Proliferation Ability for Advanced Basic Media Mesenchymal Stem Cell (ABM-M)

In order to analyze the proliferation rate of adult tissue derived mesenchymal stem cell in marrow and fat tissues of ABM-M medium, frozen marrow derived and adipose mesenchymal stem cell are purchased. Marrow derived mesenchymal stem cell is cultured in Poietics MSCGM™ Bullekit. Adipose mesenchymal stem cell is cultured in Poietics ADSC-GM™ Bullekit for comparison.

1-1. Preparation of Marrow Derived and Adipose Mesenchymal Stem Cell

After warming up the mesenchymal stem cell (originated from the marrow from a company called, Lonza) at 27 degrees and immediately defrosting it, it is put into 15 mL tube that contains 5 mL of MSCM™ medium, for centrifugation for 5 minutes at 300 g. After centrifugation, the upper solution medium is removed and ished with 10 mL of a new MSCGM medium, in order to measure the number of cells and cell survival rate. After inoculating the prepared cells about 5,000 cells/cm$^2$ in T25 flask, they are cultured at 37 degrees with 5% of CO2. A culturing solution is replaced every 3-4 days to culture, with 5 mL of MSCGM medium respectively for different culturing container. Once cells grow to take up over 90% of flask bottom area, successive culturing is carried out. Some number of cells for test purpose is prepared after 2nd, 3$^{rd}$, and 4$^{th}$ culturing process.

After warming up the mesenchymal stem cell (originated from fatty cells purchased from Lonza) at 37 degrees and immediately defrosting it, it is put into 15 mL tube that contains 5 mL of ADSC-GM medium, for centrifugation for 5 minutes at 300 g. After centrifugation, the upper solution medium is removed and ished with 10 mL of a new ADSC-GM medium, in order to measure the number of cells and cell survival rate. After inoculating the prepared cells about 5,000 cells/cm$^2$ in T25 flask, they are cultured at 37 degrees with 5% of CO2. They are cultured by replacing every 3-4 days with 5 mL of ADSC-GM medium (that contains 10% of fetal ovine serum) respectively for different culturing container Once cells grow to take up over 90% of flask bottom area, successive culturing is carried out. Some number of cells for test purpose is prepared after 2nd, 3$^{rd}$, and 4$^{th}$ successive culturing process.

1-2. Multiplication of Marrow Derived Mesenchymal Stem Cell in ABM-M Medium

The multiplication potency of ABM-M medium is investigated in the present invention, with MSCM as a control group, in comparison with marrow derived mesenchymal stem cell which is successively cultured up to 4$^{th}$ times from MSCGM medium. MSCGM medium consists of a basic medium of MSC-BM and additives ((50 mL growth supplement, 10 mL L-glutamine, and 0.5 mL penicillin-streptomy). Therefore, a test is carried out for comparison purpose by adding additivies also to ABM-M medium (Table 2).

TABLE 2

Preparation of ABM-M medium and MSCGM medium in terms of their respective multiplication rate 120.

| | Classification | Additive (Lonza) | 10% of fetal bovine serum | 2 mM L-Glutamine |
|---|---|---|---|---|
| Control Group | MSC-BM + FBS | | ○ | ○ |
| | MSC-BM + Additives | ○ | | |

TABLE 2-continued

Preparation of ABM-M medium and MSCGM medium in terms of their respective multiplication rate 120.

| Classification | | Additive (Lonza) | 10% of fetal bovine serum | 2 mM L-Glutamine |
|---|---|---|---|---|
| Test Group | ABM-M + FBS | | ○ | ○ |
| | ABM-M + Additives | ○ | | |

After 4-successive culturing, 5,000 cells/cm2 is inoculated into T75 flasks (medium composition is explained in Table 2) that contain different medium. It is kept at 37 degrees and 5% of CO2 for culturing. After culturing for 10 days changing culturing solution with different medium in culturing container every 3-4 days, the number of cells is measured.

Based on FIGS. 1 and 3, as for the control group, the medium (MSC-BM+FBS, which is added with 10% of fetal bovine serum and MSC-BM) did not show any multiplication over 10 days. For MSCGM medium (MSC-BM that is added with additives), there found almost no multiplication.

However, the medium (ABM-M+FBS, added with 10% of fetal bovine serum (FBS) onto ABM-M medium) has higher multiplication over MSCGM, and also has faster doubling time. Also, the medium (ABM-M mixed with additives) shows higher multiplication rate and faster doubling time than MSCGM. That is, it is found that the creating ABM-M medium can increase the multiplication rate of marrow derived mesenchymal stem cell.

However, in MSCGM medium, there found no multiplication of marrow derived mesenchymal stem cell. In comparison, in ABM-M medium that contains 10% of fetal bovine serum and 2 mL L-glutamine, there found an increase of marrow derived mesenchymal stem cell. This shows that the multiplication capability of mesenchymal stem cell is lost, which is cultured in MSCGM medium. However, it shows that ABM-M medium still keeps proliferation ability.

In order to check the proliferation ability in ABM-M medium, about 5,000 cells/cm$^2$ are inoculated in T150 flask to those cells that are recovered from 5th successive culturing. Then they are cultured at 37 degrees with 5% of CO$^2$. Culturing solution is replaced every 3-4 days with the ABM-M medium that contains 10% fetal bovine serum and 2 mM L-glutamine, that is cultured for 10 days. After that, as a result of checking the number of cells, there are 3,357,500 cells recovered, that shows 447% of proliferation rate, in comparison to the number of inoculation cells of 750,000. This confirms the continuing proliferation ability. Therefore, it can be concluded that ABM-M medium has an excellent proliferation ability for marrow derived mesenchymal stem cell.

TABLE 3

Analytical result on the multiplication of Mesenchymal stem cells, originated from bone marrow for respective culturing medium

| | Classification | Number of Cell Inoculation | Number of attached cells after culturing 1 day | Number of returned cells after 10 days of culturing | Doubling time (days) |
|---|---|---|---|---|---|
| Control | MSC-BM + FBS | 375,000 | 285,000 | 289,335 | 413.16 |
| Group | MSC-BM + Additives | 375,000 | 378,750 | 457,665 | 32.95 |
| Test Group | ABM + FBS | 375,000 | 360,000 | 983,500 | 6.21 |
| | ABM + Additives | 375,000 | 378,750 | 701,000 | 10.13 |

1-3. Multiplication of Adipose Mesenchymal Stem Cell from ABM-M Medium

The multiplication of the adipose mesenchymal stem cell in ABM-M medium is investigated with ADSC-GM culture as a control group. This stem cell is the one that is successively cultured 4 times in ADSC-GM medium. ADSC-GM medium consists of ADSCC-BM as a basic medium and additives (50 mL of fetal bovine serum, 5 mL L-glutamine, and 0.5 mL gentamicin-amphotercin). Therefore, 10% of fetal bovine serum and 2 mM L-glutamine are added into ABM-M medium to carry out a comparative test.

After 4-successive culturing, 5,000 cells/cm2 is inoculated into T75 flasks that contain different medium. It is kept at 37 degrees and 5% of CO2 for culturing. After culturing for 7 days changing culturing solution with different medium in culturing container every 3-4 days, the number of cells is measured. After 4-successive culturing returned cells, 5,000 cells/cm2 is inoculated into T175 flasks that contain different medium. It is kept at 37 degrees and 5% of CO2 for culturing. After culturing for 7 days changing culturing solution with different medium in culturing container every 3-4 days, the number of cells is measured.

Based on FIG. 2, 4 and Table 5, in comparison to the control group of ADSC-GM, our medium (ABM-M+FBS) that is added with 10% of fetal bovine serum onto ABM-M medium showed faster doubling time in 5$^{th}$ and 6th successive culturing. There are more returned cells. This confirmed that the multiplication rate is higher for adipose mesenchymal stem cell, due to the present invention of ABM-M medium.

TABLE 4

Analytical result on the multiplication of adipose Mesenchymal stem cells, for respective culturing medium

| | ADSC-GM | | ABM-M + FBS | |
|---|---|---|---|---|
| | Passage 5 | Passage 6 | Passage 5 | Passage 6 |
| Number of Cell Inoculation | 375,000 | 875,000 | 375,000 | 875,000 |
| Number of attached cells after culturing 1 day | 373,125 | 761,250 | 390,000 | 843,750 |
| Number of returned cells after culturing 7 day | 935,500 | 2,219,000 | 1,161,000 | 4,443,500 |
| Doubling time (days) | 4.5 | 3.9 | 3.8 | 2.5 |

Practical Example 2

Immunological Analysis of Mesenchymal Stem Cell that is Cultured in ABM-M Medium Those cells that are cultured in media such as 1-2 and 1-3 of Practical Example 2 are detached after treating them with TrypLe express. Then cell are acquired after centrifugation for 5 minutes for 400 g. Then it is ished two times with FASC solution. Those cleaned cells are divided in 5 10(5) respectively. Then they are reacted for 20 minutes with anti-CD166, CD105, CD90, CD44, CD29, CD73, HLA-ABC, CD31, CD34, CD45, CD80 and HLA-DR antibody. Then they are ished, and floated in FACS solution for analysis with flow cytometer. The analysis on the cell surface confirmed that it is mesenchymal phenotype.

As a result, similar to those mesenchymal stem cells that are cultured in MSC-GM and ADSC-GM media (control group), CD166, CD106, CD90, CD44, CD29, CD73, and HLA-ABC showed benign expression in those cells cultured in ABM-M that contains 2 mM of L-glutamine and 10% of fetal bovine serum. It is confirmed they showed the characteristics of mesenchymal stem cells because CD14, CD31, CD34, CD45, CD80 and HLA-DR showed negative expression (Table 5).

TABLE 5

Immunological Characteristics of Meseachymal stem cell that is cultured in ABM-M medium

| | Mesenchymal stem cell with the origin from bone marrow | | Mesenchymal stem cell with the origin from fatty cells | |
|---|---|---|---|---|
| | MSC-GM | ABM-M | ADSC-GM | ABM-M |
| CD29 | 76.6% | 83.2% | 88.7% | 97.7% |
| CD44 | 95.2% | 98.0% | 99.9% | 100% |
| CD73 | N/A | N/A | 98.7% | 98.5% |
| CD90 | 91.86% | 93.25% | 97.4% | 98.0% |
| CD105 | 99.6% | 98.6% | 99.9% | 100% |
| CD166 | 99.5% | 99.5% | 100% | 99.9% |
| HLA-ABC | 76.7% | 82.2% | 83.8% | 92.1% |
| CD80 | 0.0% | 0.1% | 0.2% | 0.1% |
| CD45 | 3.9% | 9.12% | 0.2% | 3.0% |
| CD34 | 0.2% | 0.1% | 5.2% | 14.6% |
| CD31 | 0.1% | 1.9% | 0.1% | 0.6% |
| CD14 | 0.2% | 0.09% | 0.8% | 3.0% |
| HLA-DR | 0.1% | 0.0% | 0.1% | 0.1% |

Practical Example 3

Differentiation Potency Analysis of Mesenchymal Stem Cell that is Cultured in ABM-M Medium Those cells that are cultured in media such as 1-2 and 1-3 of Practical Example 2 are detached after treating them with Triplex. Then cell are acquired after centrifugation for 5 minutes for 400 g, which confirmed differentiation potency in vitro.

In order to verify the differentiation potency of cultured mesenchymal stem cell, the differentiation is induced as shown below in accordance with the methodology suggested by Schallmoser K. et al., Tissue Eng Par C Method 14:185, 2008.

For the differentiation to osteogenic cells, the mesenchymal stem cells that are early-cultured in ABM-M medium is put to be cultured and differentiated again for 2-3 weeks in alpha-MEM medium that contains 10% fetal bovine serum, 10 mM beta-glycerolphosphate, 50 uM ascorbic acid and 10(−7)M dexamethasone, as shown in FIG. 8. Then whether or not alkaline phosphatase is expressed is measured by ALPase dyeing. The calcium accumulation is confirmed with von Kossa dyeing.

For the differentiation into fatty cells, the mesenchymal stem cells that are early-cultured in ABM-M medium is put to be cultured and differentiated again for 2-3 weeks in alpha-MEM medium that contains 10% fetal bovine serum, 10(−7)M dexamethasone, 100 uM indomethacin and 10 ug/mL insulin, as shown in FIG. 9. Then for confirmation purpose, fatty bubbles that are accumulated within cells are dyed with oil Red-O.

In order to induce the differentiation into cartilage cells, about 5×10(5) mesenchymal stem cells that are early-cultured in ABM-M medium are centrifuged for 5 minutes in 300 g unit to make cell clumps, as shown in FIG. 10. After that, it is cultured and differentiated again for 3 weeks in a DMEM low glucose medium that contains 10(−7) M dexamethasone, 50 uM ascorbin acid, 1 nM sodium pyruvate, 10 n/mL TGF-beta, and 100 ng/mL BMP-2. Those cartilage cells that are induced to differentiate are divided into 5 um of serial section after being put through paraffin embedding process. Then they are dyed through H/E dyeing, safranin O dyeing, alcian blue dyeing, Sirius red dyeing, COMP dyeing, collagen type II and I dyeing, which confirmed the differentiation potency.

In the present invention, after successive culturing bone marrow and adipose mesenchymal stem cell two times from ABM-M medium, and inducing them into multi-differentiation, it is compared with the control group that did not induce multi-differentiation. As a result of carrying out settling ALP dyeing and calcium settlement by inducing them into osteogenic cells, it is found that calcium settled and alkaline phaphatase is clearly expressed, in contrast to the control group which is not induced to differentiate. Also, as a result of carrying out oil Red-O dyeing after inducing into fatty-cells, it is found that they are differentiated into fatty cells in contrast to the control group that is not induced to differentiate. After inducing cartilage cells to differentiate to mesenchymal cell clumps and dyeing through safranin O dyeing, alcian blue dyeing, sirius red dyeing, COMP dyeing, collagen type II and I dyeing, it is found that glycosaminoglycan (GAG), proteglycan, collagen type I are expressed, which are similar to normal cartilages.

Practical Example 4

Karyotype Analysis of Mesenchymal Stem Cell that is Cultured in ABM-M Medium

As similar to 1-2 and 1-3 of Practical Example 1, ABM-M medium is subcultured 10 times (that contains 10% of fetal bovine serum and 2 mM of L-glutamine after separating mesenchymal stem cell from grown cell such as bone marrow and fatty tissue from other entities). Then, its karyotype of cultured mesenchymal stem cell is analyzed. Among 20 metakinesis phases, 5 metakinesis are analyzed by using GTG banding technique. Karyotype is named in accordance with International System for Cytogenetic Nomenclature (2009). Based on the 5 monitored metaphase cells, FIG. 11 shows 46 normal XY karyotypes, and FIG. 12 shows 46 normal XX karyotypes.

As described before, the Advanced Basic Media—Mesenchymal stem cell (ABM-M medium) keeps the same cell characteristics and differentiation potency of mesenchymal stem cells, in comparison to the existing mesenchymal stem cell cultured medium. Also, it is possible to get pure mesenchymal stem cell by culturing a large amount of mesenchymal stem cell, through the use of media with excellent cell growth and proliferation rate.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

The invention claimed is:

1. An Advanced Basic Media-Mesenchymal stem cell (ABM-M) culturing medium comprising:
   overlapped components which are included in two or more of Dulbecco's modification of Eagle's medium (DMEM) high glucose medium, RPMI-1640 medium, and Ham's F-12 medium, wherein a highest concentration of each of the overlapped components is selected for the ABM-M culturing medium;
   non-overlapped components which are included in only one of the DMEM high glucose culturing medium, the RPMI-1640 medium, and the Ham's F-12 medium, wherein a concentration of each of the non-overlapped components is selected for the ABM-M culturing medium; and
   same source components, comprising:
      an L-Arginine source selected from the group consisting of L-Arginine Free Base and L-Arginine Monohydrochloride;
      an L-Asparagine source selected from the group consisting of L-Asparagine Anhydrous and L-Asparagine Monohydrate;
      an L-Cysteine/Cystine source selected from the group consisting of L-Cysteine Monohydrochloride Monohydrate and L-Cystine Dihydrochloride;
      an L-Histidine source selected from the group consisting of L-Histidine and L-Histidine Monohydrochloride Monohydrate;
      a Calcium source selected from the group consisting of Calcium Chloride Dihydrate and Calcium Nitrate Tetrahydrate;
      a Ferric/Ferrous source selected from the group consisting of Ferric Nitrate Nonahydrate and Ferrous Sulfate Heptahydrate;
      a Magnesium source selected from the group consisting of Magnesium Chloride Hexahydrate and Magnesium Sulfate Anhydrous;
      a Sodium Phosphate source selected from the group consisting of Sodium Phosphate Dibasic Anhydrous and Sodium Phosphate Monobasic Anhydrous; and
      a Pyridoxal/Pyridoxine source selected from the group consisting of Pyridoxal Hydrochloride and Pyridoxine Hydrochloride.

2. The ABM-M culture medium of claim 1, further comprising Amino Acids, including L-Alanine, L-Asparagine Anhydrous, L-Aspartic acid, L-Glutamic acid, L Hydroxy-L-Proline, and L-Proline, Inorganic Salts, including Cupric Sulfate Pentahydrate, Ferrous Sulfate Heptahydrate, Sodium Phosphate Dibasic Anhydrous, and Zinc Sulfate Heptahydrate, Vitamins, including D-Biotin, P-Aminobenzoic Acid (PABA), and Vitamin B12, and Hypoxanithine, L-Glutathione Reduced, Linoleic acid, Putrescine+2HCl, Thioctic Acid, and Thymindine.

3. The ABM-M culture medium of claim 1, further comprising at least one selected among serum of embryo, calf serum, horse serum, human serum, L-glutamine, antibiotics, and antifungal.

4. The ABM-M culture medium of claim 1, further comprising 10-20% of fetal bovine serum and 2-4 mM of L-glutamine.

5. The ABM-M culture medium of claim 1, further comprising Amino Acids, including L-Arginine Monohydrochloride, L-Aspartic acid, L-Cystine Dihydrochloride, and L-Histidine Monohydrochloride Monohydrate, Inorganic Salts, including Calcium Chloride Dihydrate, Ferrous Sulfate Heptahydrate, Magnesium Sulfate Anhydrous, and Sodium Phosphate Dibasic Anhydrous, and Vitamins, including Pyridoxal Hydrochloride.

6. The ABM-M culture medium of claim 1, wherein mesenchymal stem cells cultured in the ABM-M medium express over 95% positive surface marker for CD166, CD105, CD90, CD73, and CD44, and express over 80% positive surface marker for CD29 and HLA-ABC, and express less than 5% negative surface marker for CD14, CD31, CD34, CD45, CD80 and HLA-DR.

7. An Advanced Basic Media-Mesenchymal stem cell (ABM-M) culturing medium consisting of:
   overlapped components which are included in two or more of Dulbecco's modification of Eagle's medium (DMEM) high glucose medium, RPMI-1640 medium, and Ham's F-12 medium, wherein a highest concentration of each of the overlapped components is selected for the ABM-M culturing medium;
   non-overlapped components which are included in only one of the DMEM high glucose culturing medium, the RPMI-1640 medium, and the Ham's F-12 medium, wherein a concentration of each of the non-overlapped components is selected for the ABM-M culturing medium; and
   same source components, consisting of:
      an L-Arginine source selected from the group consisting of L-Arginine Free Base and L-Arginine Monohydrochloride;
      an L-Asparagine source selected from the group consisting of L-Asparagine Anhydrous and L-Asparagine Monohydrate;
      an L-Cysteine/Cystine source selected from the group consisting of L-Cysteine Monohydrochloride Monohydrate and L-Cystine Dihydrochloride;
      an L-Histidine source selected from the group consisting of L-Histidine and L-Histidine Monohydrochloride Monohydrate;
      a Calcium source selected from the group consisting of Calcium Chloride Dihydrate and Calcium Nitrate Tetrahydrate;
      a Ferric/Ferrous source selected from the group consisting of Ferric Nitrate Nonahydrate and Ferrous Sulfate Heptahydrate;
      a Magnesium source selected from the group consisting of Magnesium Chloride Hexahydrate and Magnesium Sulfate Anhydrous;
      a Sodium Phosphate source selected from the group consisting of Sodium Phosphate Dibasic Anhydrous and Sodium Phosphate Monobasic Anhydrous; and
      a Pyridoxal/Pyridoxine source selected from the group consisting of Pyridoxal Hydrochloride and Pyridoxine Hydrochloride.

8. An Advanced Basic Media-Mesenchymal stem cell (ABM-M) culturing medium consisting of:
   Glycine at 30 mg/L; L-Alanine at 9 mg/L; L-Arginine Monohydrochloride at 211 mg/L; L-Asparagine Anhydrous at 50 mg/L; L-Aspartic acid at 20 mg/L; L-Cystine Dihydrochloride at 62.6 mg/L; L-Glutamic Acid at 20 mg/L; L-Glutamine at 584 mg/L; L-Histidine Monohydrochloride Monohydrate at 42 mg/L; L-Hydroxy-L-Proline at 20 mg/L; L-Isoleucine at 105 mg/L; L-Leucine at 105 mg/L; L-Lysine Monohydrochloride at 105 mg/L; L-Methionine at 30 mg/L; L-Phenylalanine at 66 mg/L; L-Proline at 34.5 mg/L; L-Serine at 42 mg/L; L-Threonine at 95 mg/L; L-Tryptophan at 16 mg/L; L-Tyrosine Disodium Salt Dihydrate at 103.79 mg/L; L-Valine at 94 mg/L;

Calcium Chloride Dihydrate at 265 mg/L; Cupric Sulfate Pentahydrate at 0.0025 mg/L; Ferrous Sulfate Heptahydrate at 0.834 mg/L; Magnesium Sulfate Anhydrous at 97.67 mg/L; Potassium Chloride at 400 mg/L; Sodium Chloride at 6,400 mg/L; Sodium Phosphate Dibasic Anhydrous at 142.04 mg/L; Zinc Sulfate Heptahydrate at 0.863 mg/L;

Ascorbic Acid Phosphate at 50 mg/L; Choline Chloride at 13.96 mg/L; D-Biotin at 0.2 mg/L; D-Ca Pantothenate at 4 mg/L; Folic Acid at 4 mg/L; Myo-Inositol at 35 mg/L; Nicotinamide at 4 mg/L; P-Aminobenzoic Acid at 1 mg/L; Pyridoxal Hydrochloride at 4 mg/L; Riboflavin at 0.4 mg/L; Thiamine Hydrochloride at 4 mg/L; Vitamin B12 at 1.36 mg/L;

D-glucose Anhydrous at 4,500 mg/L; Hypoxanthine at 4.08 mg/L; L-Glutathione Reduced at 1 mg/L; Linoleic Acid at 0.084 mg/L; Phenol Red Sodium Salt at 15.9 mg/L; Putrescine+2HCl at 0.161 mg/L; Sodium Pyruvate at 110 mg/L; Thioctic Acid at 0.21 mg/L; and Thymidine at 0.73 mg/L.

* * * * *